United States Patent [19]

Witkin

[11] Patent Number: 5,035,883

[45] Date of Patent: Jul. 30, 1991

[54] COMPOSITION AND METHOD FOR TREATING HUMAN DISORDERS SUSCEPTIBLE TO ANTIMICROBIAL TREATMENT

[75] Inventor: Roy T. Witkin, Westport, Conn.

[73] Assignee: Albert L. Jacobs, New York, N.Y.; a part interest

[21] Appl. No.: 452,280

[22] Filed: Dec. 15, 1989

Related U.S. Application Data

[63] Continuation of Ser. No. 239,799, Sep. 2, 1988.

[51] Int. Cl.$^5$ .................... A61K 33/40; A61K 31/79; A61K 33/18; A61L 9/00
[52] U.S. Cl. ........................................ 424/78; 424/80; 424/667; 424/668; 424/613; 422/29; 422/37
[58] Field of Search ................... 424/78, 80, 667, 668, 424/51, 53, 433, 613, 430; 422/29, 37

[56] References Cited

U.S. PATENT DOCUMENTS

| | | | |
|---|---|---|---|
| 2,739,922 | 4/1956 | Shelanski | 424/667 |
| 4,592,488 | 6/1986 | Simon et al. | 424/51 |
| 4,738,840 | 4/1988 | Simon et al. | 424/613 |

Primary Examiner—John Doll
Assistant Examiner—P. I. Curtis
Attorney, Agent, or Firm—Rosenman & Colin

[57] ABSTRACT

An antimicrobial composition for the treatment of non-oral and non-periodontal human disorders due to infectious microorganisms susceptible to antimicrobial treatment and wherein the composition is an aqueous or aqueous alcoholic solution of povidone iodine complex to which nascent oxygen is supplied and the resulting admixture being freshly applied to the said disorders.

2 Claims, No Drawings

COMPOSITION AND METHOD FOR TREATING HUMAN DISORDERS SUSCEPTIBLE TO ANTIMICROBIAL TREATMENT

This is a continuation of Ser. No. 239,799 filed Sept. 2, 1988.

THE PRESENT INVENTION

This invention relates to a composition and method for the treatment of a broad scope of human disorders due to infectious microorganisms. The composition comprises an aqueous solution of the povidone iodine complex containing nascent oxygen from a supply source thereof. The composition has enhanced cidal activity against microorganisms including staphylococcus, streptococcus, pseudomonas, enteric bacteria, molds, yeast, selected viruses, trichomonas, actinomyces and bacteroides.

BACKGROUND OF THE INvENTION

It is known from U.S. Pat. No. 4,521,403 issued June 4, 1985 of which I am a co-inventor that the relatively weak antimicrobial activity of iodine in the form of a povidone iodine complex can be greatly enhanced by the presence of nascent oxygen from any suitable supply source such as a peroxide like $H_2O_2$. Within certain designated relative proportions the nascent oxygen interacts with or upon the iodine derived from the povidone iodine complex and a greatly enhanced antimicrobial activity is obtained. As noted in that patent the combination of povidone iodine complex and nascent oxygen in aqueous or aqueous alcoholic solution is particularly advantageous in the treatment of periodontal diseases. There is no teaching or suggestion, however, that the cidally enhanced composition has other and unrelated uses and the present invention is directed thereto.

DETAILS OF THE INVENTION

Since iodine is only very slightly soluble in water in its elemental form its antimicrobial activity is inadequate to treat or overcome various human disorders due to infectious microorganisms and which are susceptible to antimicrobial treatment. While iodine is soluble in alcohol and is available in the form of tincture of iodine such has not been found to be useful for the purposes of the present invention and the amount of antimicrobial activity in tincture of iodine is small.

It has now been discovered that the antimicrobial activity of iodine can be enhanced or synergized by converting it to a povidone iodine complex which is freely soluble in water and then incorporating therein nascent oxygen from any suitable source or supply such as a peroxide like $H_2O_2$. A freshly prepared composition of these components has a very high degree of antimicrobial activity against a wide spectrum of infectious microorganisms which are susceptible to antimicrobial treatment. Preparatory to the preparation of the aqueous or aqueous alcoholic solution of the povidone complex and the incorporation therein of nascent oxygen such as that supplied by $H_2O_2$ or other suitable peroxide the components must be kept physically separated and this is conveniently carried out by means of a compartmented container or receptacle having a partition or barrier wall arrangement in order that the components shall be kept uncombined prior to the time when it is desired to combine them and apply them to the human disorders.

As stated above the microorganisms which are very susceptible to the cidal potential of the combined components are exemplified above and the particular microorganisms used for the treatment of a designated disorder is selected accordingly and the human disorders which can be thereby destroyed or overcome can be divided in a number of categories.

EXAMPLE 1

The above invention is found to be particularly useful in the field of dermatology and in the treatment of Acne
Athlete's Foot (Tinea Pedis)
Ring Worm (Tinea Corporis)
Impetigo
Fungal Infections
Jock Itch (Tinea Cruris)
Folliculitis The current treatment for acne is an ointment or cream using benzoyl peroxide as the active ingredient. My research to date has already shown that the combination of the active agents, in liquid or other form (ointment, salve or cream), is more effective on the bacterial targets than any individual peroxide working alone. The chief bacterial agent indicated is common staph.aureus.

The organisms involved in athlete's foot infection are yeast and fungi. A bath, cream or ointment aimed at athlete's foot or any other similar fungus infection using the two-component system would be highly microcidal and effective.

The addition of non-active ingredients makes the composition a very powerful medicated shampoo, used against bacterially caused dandruff and other infestations, mites, ticks, etc. (Superficial mycoses (Dermatophytoses).

The preferably freshly prepared antimicrobially enhanced composition is applied in any appropriate or known manner depending upon the particular dermatological disorder. Usually the composition is swabbed, washed, rinsed or otherwise contacted with the affected area and it is thereby clear to those skilled in the art how the treatment is carried out. It is understood that if necessary the treatment can be repeated particularly if the disorder recurs.

EXAMPLE 2

The invention has been found to be particularly useful in the treatment of mucous membrane infections such as vaginal yeast infections and throat infections and the manner of applying the composition for the overcoming of these infections will be clear to those experienced in those arts.

The mucous membranes of the vaginal tract and those of the mouth are quite similar in make-up, function and susceptibility to analogous infection. A perinatal clinic at a major New York City Hospital has successfully used the present formulation to control herpetic infections of pregnant women by simple in-office instillation on vaginal cotton sponges.

Monilial infections, a very common vaginal disorder has been shown to lend itself to treatment with the combined product.

EXAMPLE 3

The composition has been found to be very effective against selected viral infections such as herpes simplex I or papilloma viruses.

EXAMPLE 4

The composition has been found to have excellent antimicrobial activity in the treatment and overcoming of a variety of infections which are of the nature of a general sanitizing and debriding action and examples thereof are:

human first-aid debriding and disinfecting injuries
sterilization of food industry equipment
sanitization/sterilization of bio-medical machines i.e. dialysis and heart-lung units.

In the present invention it has been found further that the relative proportions of povidone iodine complex and nascent oxygen are not critical and may be adjusted to the particular human disorder being treated. Some of these human disorders being of a more serious nature require a higher concentration of components in the composition whereas others and much less serious infections can be treated with a very mild or relatively dilute composition especially where sterilization is to be carried out in equipment such as those of Example 4 although it will be quite clear that the concentration must be sufficient in the freshly prepared solution to ensure that all infectious microorganisms susceptible to antimicrobial treatment are destroyed or rendered ineffective. Thus the freshly prepared aqueous and aqueous alcoholic solution comprises dissolved povidone iodine complex from which the iodine is derived and the nascent oxygen supplied from $H_2O_2$ or other sources may be varied as to concentration which may range from a low or dilute concentration of the order of about 0.1% to about 0.5% to a greater concentration for the treatment of more serious human disorders which are more difficult to treat and in such instances the concentrations may range from about 0.5% to 10%. The concentration of the iodine derived from the povidone iodine complex is calculated on the basis of the weight of the solution and the nascent oxygen present in the freshly prepared antimicrobial solution is calculated on the basis of the weight of $H_2O_2$. The povidone iodine complex is a brownish powder as usually prepared and therefore can be readily stored without material decomposition or loss of potency in a compartment of a receptacle or package having a physical barrier between the compartments. $H_2O_2$ exists in a number of concentrations but it has been found that the concentration should not exceed about 10% by weight as more highly concentrated $H_2O_2$ solutions are irritating and are capable of attacking mucous membrane. Such is the case with $H_2O_2$ of 40% concentration.

It will be clear from the foregoing that the antimicrobial composition of the present invention and its use thereof in treating human disorders susceptible to antimicrobial treatment that the invention is of very versatile nature and can constitute or form a part of a number of compositions for the treatment of a wide variety of human disorders as illustrated by the following medical considerations useful as a topical spray to prevent infection from superficial cuts, scrapes and bruises and as a home remedy for minor infections for the treatment of scratches, scrapes and cuts and of punctures of the human skin. Such as those listed below:

PRE-SURGICAL SCRUB: Currently povidone-iodine is being used as a pre-surgical scrub, my product would provide a greater degree of efficacy on both the surgeon's hands and the area to be surgerized.

It will thus be appreciated that iodine derived from a povidone-iodine complex has its relatively minor antimicrobial activity greatly enhanced by supplying nascent or active oxygen to an aqueous or aqueous alcoholic solution of the PVO-I complex from a suitable or convenient supply source such as the $H_2O_2$ or other nascent oxygen source, that the PVP-I and nascent oxygen e.g. $H_2O_2$ are maintained out of physical contact with one another in a compartmented or partitioned container or receptacle and that they are combined shortly prior to use and applied to overcome the human disorder which is susceptible to antimicrobial treatment. The invention resides in the composition ready for use and in the treatment of a wide spectrum of microbial infections.

What is claimed is:

1. A method of treating vaginal infection, athlete's foot infection, herpes simplex I and papilloma virus infection and method of human first aid debriding and disinfecting injuries due to microbial infections which comprises applying to affected human area a composition comprising an aqueous solution of povidone-iodine complex containing nascent oxygen from a suitable supply source thereof, and povidone iodine complex solution being maintained out of physical contact with the nascent oxygen source and combined shortly prior to application of the composition to the microbially affected human area thereby providing maximal antimicrobial activity while shortening the treatment time and increasing its effectiveness.

2. A method of treating infections of claim 1, which comprises spraying, swabbing, washing, shampooing, and otherwise applying to the infected body area of said composition.

* * * * *